(12) United States Patent
Johannesen

(10) Patent No.: US 6,567,173 B1
(45) Date of Patent: May 20, 2003

(54) OPTICAL PRESSURE SENSOR

(75) Inventor: Kjetil Johannesen, Trondheim (NO)

(73) Assignee: Leiv Eiriksson Nyfotek AS, Trondheim (NO)

( * ) Notice: Subject to any disclaimer, the term of this patent is extended or adjusted under 35 U.S.C. 154(b) by 0 days.

(21) Appl. No.: 09/622,715

(22) PCT Filed: Dec. 9, 1998

(86) PCT No.: PCT/NO98/00370

§ 371 (c)(1),
(2), (4) Date: Aug. 22, 2000

(87) PCT Pub. No.: WO99/45352

PCT Pub. Date: Sep. 10, 1999

(30) Foreign Application Priority Data

Mar. 6, 1998 (NO) .............................................. 1012/98

(51) Int. Cl.[7] .................................................. G07B 9/02
(52) U.S. Cl. ..................................................... 356/480
(58) Field of Search ................................ 356/480, 517, 356/35.5, 481; 250/227.17, 227.19

(56) References Cited

U.S. PATENT DOCUMENTS 5,392,117 A * 2/1995 Belleville et al. ........... 356/480
5,395,405 A * 3/1995 Nagel et al. ................ 356/35.5

* cited by examiner

Primary Examiner—Samuel A. Turner
Assistant Examiner—Patrick Connolly
(74) Attorney, Agent, or Firm—Rothwell, Figg, Ernst & Manbeck

(57) ABSTRACT

An optical pressure sensor includes an optical fiber having a well defined end part and a casing having a cylindrically shaped cavity with an inner diameter that is essentially the same as the outer diameter of fiber. The end of the optical fiber is positioned at a chosen axial position inside the cavity, thereby closing one end of the cavity. A body is positioned in the cavity and has a first, at least partially, reflective surface. The partially reflective surface, fiber, and casing define a chamber. The chamber contains a compressible fluid. At least one of the body and the optical fiber is movably connected to the casing in the axial direction thus to provide a pressure coupling between the chamber and the environment.

7 Claims, 1 Drawing Sheet

OPTICAL PRESSURE SENSOR

BACKGROUND AND SUMMARY OF THE INVENTION

This invention relates to an optical pressure sensor comprising an optical fibre or waveguide with a well defined end part, and a casing having a cylindrical cavity with essentially the same transversal dimensions as the optical fibre, the end of the optical fibre being positioned at a chosen axial position inside the cavity thus to close one end of the opening.

Today there are a number of different types of pressure sensors based on different types of membranes which can be bent and read using electrical conductivity, capacitance or optical measuring of the distance between a part of the membrane or an element connected thereto, and an optical fibre.

There are a plurality of techniques for reading this types of distances, using white-light interferometry which may read the distance without ambiguity, but with moderate resolution. It may be measured with interferometric techniques having high coherence which provides large sensitivity for changes in the distance, but has an inherent ambiguity in the measurement. These techniques may be combined, e.g. by simultaneous use of coherent light with different wavelengths.

The measuring techniques are common knowledge, and may even to a certain extent be bought as commercially available instruments.

The optical measuring techniques has the following advantages:
  Potentially good resolution.
  Unaffected by electromagnetic influences, such as electromagnetic pulses etc.
  Secure against electrical discharges/igniters, which make them useful in medical applications, and in uses related to explosives and inflammable environments.
  Potentially very compact, especially in relation to light guides.

Membrane based optical sensors are usually expensive and relatively large. Mounting of a membrane against an optical fibre requires precision and, as the membrane responds to all movements the surrounding construction must be very rigid, while the membrane must be very deformable, especially to low pressures. This type of solution is usually expensive, partially because of the costs related to the probe production. The present invention has a potential of being an inexpensive and also very compact solution.

Swedish patent No. 462,631 shows a variant of the known art comprising a membrane coupled to a reflective part which may be moved down in front of the end of an optical fibre. The amount of light being reflected back thus depends upon the pressure affecting the membrane.

The solution described in the Swedish patent is relatively compact and may e.g. be used in medical applications, but has a limited sensitivity, as it is not based on interferometry.

DE 40.35.373 describes a Fabry-Perot interferometer positioned at the end of an optical fibre. It is not mentioned how the interferometer is made, but it will most likely come into the abovementioned category of relatively expensive solutions. Also the partially reflective surfaces in this interferometer has limited possibilities for relative movements, which will result in either a limited dynamic range or a limited resolution.

The German patent publication also describes an example of the use of such an interferometer, and a method for calculating the pressure based on the measurements.

Another type of sensors based on optical fibres known in the art uses two optical fibres fastened end to end in a casing. Deformations in this casing may be measured as it affects the distance between the fibre ends. This system is relatively rigid and is not suitable for measuring pressure, but is used for measuring tension.

The object of this invention is thus to provide a miniature pressure probe being inexpensive in production and at the same time maintains the possibilities of the fiberoptic systems for making exact measurements. The pressure probe must be sufficiently small to be used in medical applications, e.g. put into the blood stream of a patient. This obtained using an optic pressure sensor as described above being characterized in that a body is positioned into the cavity, said body having a first at least partially reflective surface, said partially reflective surface, fibre and casing delimiting a chamber, said chamber containing a compressible fluid, and in that at least one of the body and the optical fibre is movably connected to the casing in the axial direction thus to provide a pressure coupling between the chamber and the environment.

This way a simple Fabry-Perot interferometer is obtained in which the external pressure moves a movable body with a partially reflective surface toward or away from a partially reflective end of an optical fibre or light guide, thus affecting the distance between the mirrors in the resonator.

According to an especially preferred embodiment of the invention the first optical fibre is fastened to the casing, while the movable body is a second optical fibre being loosely positioned in the casing. The chamber is sealed using the capillary effect between the second optical fibre and the casing, either by placing a liquid, e.g. silicone oil, at the outer end of the fibre, or possibly second fibre, and let it be drawn into space between them, or possibly the liquid in which the pressure is to be measured may be drawn into the intermediate space. The liquid layer between the body and the casing provides, in addition to sealing the chamber, a lubricating effect and reduces the friction between them. This increases the precision and the speed of the measurements. In addition the sensitivity of the sensor may be adjusted by simply adjusting the distance between the fibres before use by controlling the amount of fluid being positioned in the chamber.

BRIEF DESCRIPTION OF THE DRAWINGS

The invention will be described below with reference to the accompanying drawings, which illustrate examples of embodiments of the invention.

DETAILED DESCRIPTION OF THE INVENTION

Figure 1:
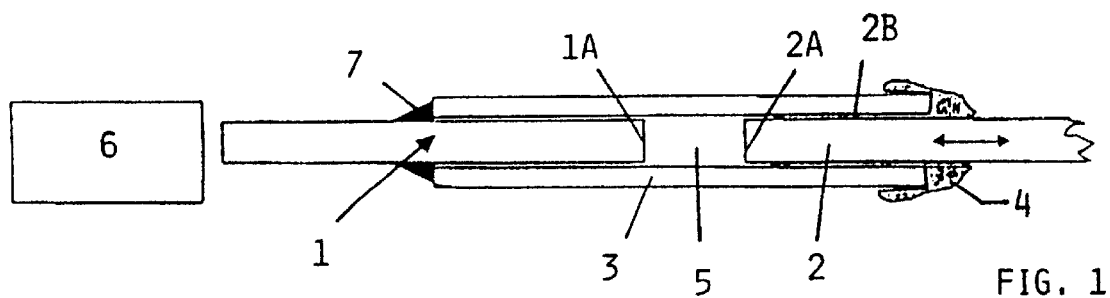
FIG. 1 shows a cross section of a preferred embodiment of the invention.

According to the embodiment of the present invention as shown in FIG. 1 the first optical fibre end 1 is positioned inside a casing 3 and defines together with a body 2 a chamber 5. Both the surface 1A on the fibre end 1 and the surface 2A on the body 2 is partially reflective so that the chamber 5 thus constitutes a Fabry-Perot interferometer.

The end part 1A of the optical fibre 1 is well defined, which means that it is formed in such a way that the light output and input at the fibre end is controlled. For example the end part 1A may be flat or may be shaped as a lens in order to focus the light. The chosen solution will among other things depend on the shape of the end part 2A of the body.

The chamber contains a gas or possibly a compressible liquid having a refractive index different from the refractive index of body 2 and the first optical fibre 1 if the mirrors 1A, 2A are only constituted by the surfaces between the different materials and fluids.

The first optical fibre 1 is at its other end connected to measuring equipment 6 of per se known type, e.g. as described in the abovementioned German patent publication. This equipment is not a part of this invention and will not be described in any detail here.

In order to keep the casing 3 in the correct position the first optical fibre 1 is fastened, e.g. using cyanoacrylate 7, to the casing. It is, however, not necessary to keep the end 1 of the optical fibre in exactly the same position and the casing may therefore alternatively be fastened in other ways, e.g. to the fibre cladding, so that the fibre "floats" relative to the casing what is important in this regard is that the casing is not shifted sufficiently to open the chamber 5.

An alternative solution is the symmetrical solution in which the body 2 is fastened to the casing, while the fibre 1 may move as a response to pressure changes.

The casing 3 may be made from a number of different materials, but it preferably has a certain rigidity, so as not to be compressed by and affect the pressure inside the chamber 5, and thus the distance between the mirrors 1A,2A.

In FIG. 1 the body 2 is constituted of a second optical fibre having a suitable second end part. A liquid 4, e.g. silicone oil, positioned by the end of the casing related to the second optical fibre 2, and the capillary forces draw the liquid into the space 2B between the second optical fibre 2 and the casing 3.

The liquid 4 thus make a seal for the chamber and a lubricating layer which eases the second optical fibre's movements. A corresponding liquid may be used to lubricate the connection between the casing and the first optical fibre, if it is not fastened.

If the medium in which the pressure is to be measured contains a suitable liquid the liquid 4 may be omitted. The surrounding liquid will be drawn into the mentioned space 2B and function in a similar way.

In special cases the surrounding liquid may be drawn into the casing 3 amd consititute the body 2, so that the sensor itself, before it is positioned in the fluid, only consists of the casing 3 and the first optical fibre 1.

Figure 2:
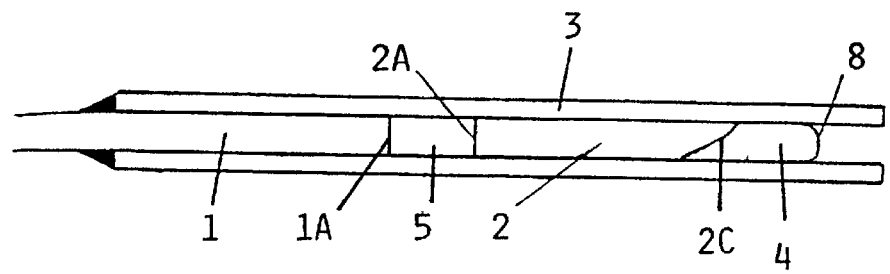
FIGS. 2–5 show cross sections of alternative embodiments of the invention.

In FIG. 2 a fibre bit 2 is completely inside by the casing. The second end 2C of the fibre bit is cut with an angle so as to avoid unwanted reflections in the interferometer. The inert liquid 4 covers the second end 2C of the fibre bit, and makes a border surface 8 toward the surrounding medium. When measuring in an aqueous environment the inert liquid is preferably hydrophobic, e.g. an oil. The opposite applies when measuring in an oily environment.

Figure 3:
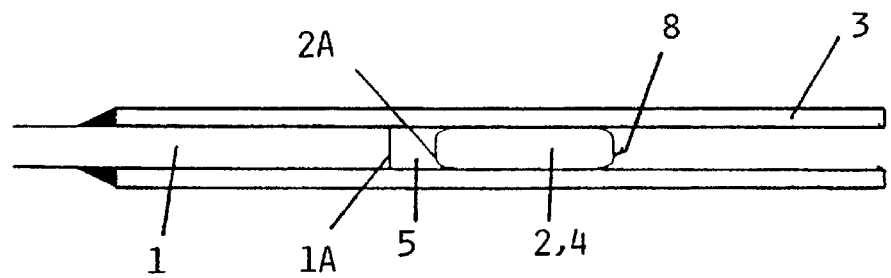

FIG. 3 shows a similar solution in which the body 2 is constituted by the liquid. This liquid is also preferably inert and makes a border surface toward the surroundings. The surface facing toward the optical fibre 1 provides a partially reflective mirror because of the difference between the refractive indices of the gas in the chamber and the liquid. As the corresponding difference between the refractive index of the of the inert liquid and the environment and the surroundings is less at the second surface 8, the reflections from this surface will be less. Unwanted reflections of this type may also be filtered out using signal treatment, as the length of the chamber will be pressure dependent, while the length of the body 2 normally will be constant. If the body 2 is not a light guide the reflections of the second end may easily be removed by providing the body 2 with a sufficiently large length to let the light be scattered or absorbed before it returns to the chamber.

Figure 4:
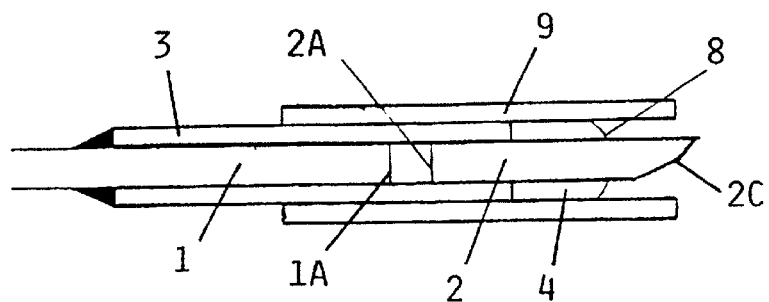
Figure 5:
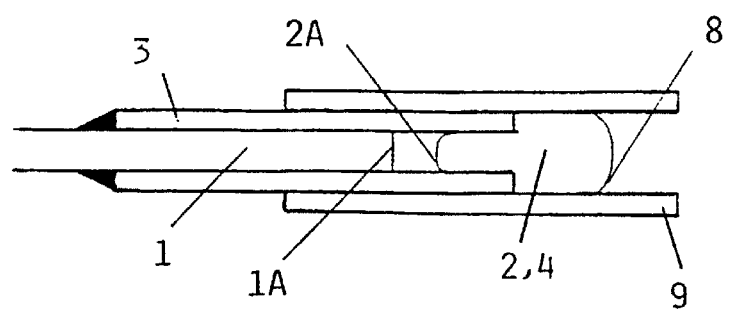

FIGS. 4–5 show a device which also comprises an outer casing 9. This gives the casing a larger diameter at the end, thus reducing the probability of it being blocked.

A number of different embodiments are possible within the scope of the invention. The end or ends of the optical fibres may be plane or may be curved so as to focus the light, and different mirrors, especially dielectric mirrors, may be provided at the ends to control the reflection characteristics, e.g. when using different wavelengths.

In the drawings the mirror surfaces 1A,2A shown as the surfaces of the first fibre end 1 and the body 2 are facing each other. It is, however, clear that other mirrors may be used, e.g. the opposite side of the body 2 or a mirror positioned within the body 2. Two mirrors, possibly both ends of the body 2, may be used simultaneously to provide a reference distance inside the sensor.

The liquid 4 being used is supposed to have little evaporation or diffusion into the fluids it comes into contact with in the chamber or the surroundings, so that it does not change it size or evaporate away. This latter may especially be relevant if the liquid constitutes the body 2, as is shown in FIGS. 3 and 5.

Since the volume of the chamber 5 may vary relatively freely the sensor may also be used as an indirect temperature sensor under otherwise stable pressure conditions.

The materials used will depend upon the application. The casing will, as mentioned, preferably be made from a rigid material, while the optical fibre or fibres will usually be made from glass, but plastic is also possible. The same applies to the dimensions of the sensor. The invention is here described by referring to optical fibres, but other types of light guides are of course also possible. Normally optical fibres will be used, with outer dimensions within the range of 80 $\mu$m to 125 $\mu$m for single mode fibres and up to 2 mm for multimode fibres.

The cladding of the optical fibres may of any known type, and is not important to this invention.

What is claimed is:

1. Optical pressure sensor comprising an optical fibre (1) having a well defined end part (1A) and a casing (3) having a cylindrically shaped cavity with essentially the same diameter as the optical fibre (1), the end (1A) of the optical fibre being positioned at a chosen axial position inside the cavity thus to close one end of the cavity, characterized in a body (2) positioned in the cavity having a first at least partially reflective surface (2A), said partially reflective surface (2A), fibre (1) and casing (3) defining a chamber (5), said chamber containing a compressible fluid, said chamber (5) being at least partially sealed by a liquid (4), and whereby the position of said partially reflecting surface (2A) depends on the hydrostatic pressure within the chamber (5), and where at least one of said body (2) and the optical fibre (1) being movably connected to the casing in the axial direction in that at least a part of the said liquid (4) forms a lubricating layer in the connection with said casing (3) by at least partially filling the space (2B) between the body (2) and the casing (3), thus to provide a pressure coupling between the chamber (5) and the environment.

2. Pressure sensor according to claim 1, characterized in that the body (2) is a second optical fibre having essentially the same diameter as the cavity, and that the space between the second optical fibre and the casing contains a liquid.

3. Pressure sensor according to claim 2, characterized in that the second optical fibre (2) is completely inside the casing, and that the pressure sensor at the outer end of said second fibre, facing the second end of the casing, comprises an inert liquid (4).

4. Pressure sensor according to claim 1, characterized in that said body (2) is a liquid (2,4).

5. Pressure sensor according to claim 4, characterized in that the liquid (2,4) constitutes a limited volume completely contained by the casing.

6. Pressure sensor according to claim 4, characterized in that the liquid (2,4) is inert.

7. Pressure sensor according to claim 1, characterized in that said liquid (4), said partially reflecting surface (2A), said body (2) and said lubricating layer are a single liquid body (2) where said partially reflecting surface (2A) is a surface of the said single liquid body (2).

* * * * *